US 6,513,931 B1

(12) United States Patent
Torrey et al.

(10) Patent No.: US 6,513,931 B1
(45) Date of Patent: Feb. 4, 2003

(54) METHOD AND APPARATUS FOR TESTING THE VISION OF A VIDEO DISPLAY TERMINAL USER

(75) Inventors: Jonathan G. Torrey, Portland, OR (US); David C. Squire, Beaverton, OR (US)

(73) Assignee: PRIO Corporation, Beaverton, OR (US)

( * ) Notice: Subject to any disclaimer, the term of this patent is extended or adjusted under 35 U.S.C. 154(b) by 38 days.

(21) Appl. No.: 09/585,895

(22) Filed: May 31, 2000

(51) Int. Cl.[7] .............................................. A61B 3/02
(52) U.S. Cl. ...................................................... 351/243
(58) Field of Search .................................. 351/211, 212, 351/216, 217, 218, 221, 237, 239, 243, 246; 600/558, 431

(56) References Cited

U.S. PATENT DOCUMENTS

| 1,306,734 | A | | 6/1919 | Armbruster | |
|---|---|---|---|---|---|
| 4,249,825 | A | * | 2/1981 | Shapiro | 600/558 |
| 4,550,990 | A | | 11/1985 | Trispel et al. | 351/243 |
| 4,572,630 | A | | 2/1986 | Task et al. | 351/243 |
| 4,576,454 | A | | 3/1986 | Charney et al. | 351/243 |
| 4,998,820 | A | | 3/1991 | Salibello et al. | 351/243 |
| 5,094,521 | A | | 3/1992 | Jolson et al. | 351/210 |
| 5,191,367 | A | | 3/1993 | Salibello et al. | 351/243 |
| 5,325,136 | A | | 6/1994 | Salibello et al. | 351/243 |
| 5,440,360 | A | | 8/1995 | Torrey et al. | 351/239 |
| 5,515,118 | A | | 5/1996 | Torrey et al. | 351/239 |
| 5,825,456 | A | | 10/1998 | Tabata et al. | 351/201 |
| 5,889,577 | A | * | 3/1999 | Kohayakawa | 351/211 |
| 5,929,972 | A | | 7/1999 | Hutchinson | 351/237 |
| 6,018,339 | A | | 1/2000 | Stevens | 345/334 |
| 6,152,565 | A | * | 11/2000 | Liu et al. | 351/212 |
| 6,238,049 | B1 | | 5/2001 | Griffin et al. | 351/243 |
| 6,260,970 | B1 | * | 7/2001 | Horn | 351/246 |

FOREIGN PATENT DOCUMENTS

| JP | 58-068784 | 4/1983 | G09F/9/00 |
|---|---|---|---|
| JP | 60-131589 | 7/1985 | G09F/9/30 |
| WO | WO 96/32880 | 10/1996 | A61B/3/02 |
| WO | WO 00/13572 | 3/2000 | A61B/3/02 |

OTHER PUBLICATIONS

PCT International Search Report dated Nov. 29, 2001 for International Application No. PCT/US01/17907.

* cited by examiner

*Primary Examiner*—George Manuel
(74) *Attorney, Agent, or Firm*—Stoel Rives LLP (57) ABSTRACT

This invention is a programmable vision testing apparatus and method for use in conducting optometric examinations of video display terminal (VDT) users. The apparatus uses a digital display screen accurately to represent a VDT used under actual work conditions. Further, a plurality of images can be displayed via the vision testing apparatus to provide a convenient and efficient way to test the eyes of VDT users with a wide variety of individual needs.

7 Claims, 9 Drawing Sheets

METHOD AND APPARATUS FOR TESTING THE VISION OF A VIDEO DISPLAY TERMINAL USER

TECHNICAL FIELD

The present invention relates to a method and apparatus for use in optometric examinations of video display terminal users.

BACKGROUND OF THE INVENTION

An increasing number of people spend many hours a day looking at a video display terminal (VDT), such as a computer screen monitor. Whether used for business, entertainment, pleasure, research, or other reasons, prolonged time spent focusing on a VDT screen can lead to considerable eye strain. As the use of VDTs becomes even more widespread, so too does the number of ophthalmological afflictions caused by their use. These afflictions are often manifested as headaches, neck or shoulder pain, tired eyes, color fringes, blurred vision, double vision, changes in spectacle prescription over time, or loss of focus. The alphanumeric and graphic character images comprising VDT images are made up of pixels that do not have clearly defined borders. The eye muscles of accommodation constantly try to bring these images into focus, causing strain on the eyes.

VDT users typically maintain a constant distance of approximately 40–60 centimeters from a VDT. The constant distance forces prolonged use of the same eye muscles, resulting in significant amounts of stress and fatigue on the eyes. These characteristics of VDT use, aggravated by the many hours that VDT users spend looking at VDTs, cause peculiar eye problems requiring prescription spectacles specifically selected to treat and prevent the afflictions of VDT users.

To determine an effective prescription for VDT users, test equipment and procedures must be implemented to simulate actual use of a VDT. A prescription for reliable corrective lenses cannot accurately be determined without examining the eyes under conditions that accurately simulate those encountered by VDT users.

The traditional process used by medical practitioners to assess the need for corrective lenses involves placing an apparatus in front of the patient that enables the doctor to change lenses while simultaneously asking the patient to choose which lens performs the best. As the doctor changes lenses, the patient looks through the apparatus to focus on a test image. Through essentially a trial and error process, the doctor determines a combination of lenses and a prescription that provides the greatest relaxation for the eye muscles. However, if the image upon which the doctor has the patient focus does not accurately simulate the actual conditions the patient experiences, the prescription cannot be determined reliably. Traditional forms of testing equipment, including nearpoint cards and projections on walls, do not provide satisfactory simulation of actual conditions for VDT users. A doctor is reduced to essentially making an educated guess as to the prescription, letting the patient use the prescription spectacles to determine if they are satisfactory. If they are not satisfactory, the patient then has to return to the doctor and the process is repeated until a satisfactory prescription is achieved. This process is inefficient, wasting valuable time and energy.

An adequate vision test for VDT users should solve at least three main problems. The first problem is one of providing the doctor flexibility. A vision test must be sufficiently flexible to allow a doctor to examine patients with a wide variety of individual needs. The second problem is one of adequately simulating a VDT. The vision test should accurately simulate the actual work conditions of VDT users. Solving this second problem requires a testing apparatus that forces the patient's eyes to act as they would when focusing on a VDT. Solving the problem of accurate simulation is made possible if the patient is in the same relative position they would be in when using a VDT (i.e., the same distance from the screen, etc.), and if the test image accurately simulates a VDT display. The third problem that must be solved is the problem of accurate, objective evaluation. Solving this third problem is accomplished though retinoscopy. Retinoscopy involves using a retinoscope objectively to measure the refractive status of the eyes.

To be effective, retinoscopy requires reducing the off-axis angle during the examination. The term "off-axis angle" refers to the angle between the line segment from the patient's eye to the patient's focal point on the test image, and the line segment from the patient's eye to the doctor's retinoscope. This allows the doctor to examine the patient from a point substantially along the line of sight from the patient to the test image. In order to obtain an accurate, objective evaluation of the patient's eyes, the doctor's retinoscope should be within approximately one inch of the test image. Using the retinoscope at a location that provides a small off-axis angle is what allows for an objective evaluation of the patient's prescription needs. If the off-axis angle is too large, the doctor cannot use the retinoscope for an objectively accurate evaluation. The alternative is the subjective process of having the patient try test lenses and report which prescription functions the best. This subjective evaluation does not afford the same accurate results as the objective evaluation though proper use of a retinoscope at a reduced off-axis angle.

Vision testing systems currently available do not provide an economical, reliable, compact, or simple-to-use solution to all three of these problems. Even existing systems designed specifically for conducting optometric exams on VDT users do not completely solve the problem of adequate simulation. Although they do place the testing screen a distance from the patient that represents VDT use, they do not provide the most accurate simulation of a modern, high-resolution VDT display. Examples of such systems include those represented by U.S. Pat. Nos. 4,576,454; 4,998,820; 5,191,367; and 5,325,136.

One of the biggest limitations on previous eye-testing systems is that they provide little flexibility for doctors to meet patient needs. They are limited to one static, fixed image. Most VDT users are subject to continually changing images, constantly forcing the eye to refocus on new characters. Without being able to change an image, a doctor cannot accurately simulate actual VDT use. Using one static image also prevents efficient testing of VDT users who have special needs, such as children or others who do not read well, and people whose reading proficiency is in another language. To accommodate such users would require physically changing the actual apparatus and substituting it with another specialized apparatus specifically designed to accommodate that patient's needs. In addition to the time wasted physically switching apparatuses, a doctor would have to purchase, maintain, and store as many different types of apparatuses as necessary to meet the individual needs of patients. To do so, a doctor would incur significant expense and inconvenience.

While there are vision testing apparatuses that use computer screens (and therefore accurately represent the display of a VDT), those systems are not specifically designed to determine prescriptions for use with VDTs, and they do not simulate actual working conditions of a VDT user. One such system is the AcuityMax computer software program produced by Science20/20. That product is not cost effective because it requires a dedicated computer (or the manufacture will not guarantee support). Accordingly, a doctor is forced pay for an entire computer system for the sole purpose of testing vision. Also, that product is not designed to test VDT users for the purpose of determining a prescription for use with a VDT. AcuityMax is only used in acuity testing to take the place of a standard acuity projector. It is used at a distance of 8 to 24 feet from the patient, not at a distance representative of VDT use. Because the software allows a computer to replace an acuity projector, rather than using the computer to adequately simulate a VDT work environment, it is ineffective in solving the problems encountered in deriving an effective prescription for VDT users.

Therefore, it is the object of the present invention to provide an improved method and apparatus for examining the eyes of VDT users. The present invention provides doctors a more flexible, realistic, and accurate system for determining the best prescriptions for VDT users.

SUMMARY OF THE INVENTION

As illustrated through one embodiment, the present invention generally comprises a vision testing method and apparatus for use in optometric examinations to simulate the actual conditions encountered by a VDT user and to facilitate prescribing corrective lenses that will perform well for a patient using a VDT. The invention is economical, reliable, compact, and simple to operate. One feature of this invention solves the problems of providing doctors flexibility and accurately simulating a VDT display by implementing a programmable digital display screen. As used throughout this specification and the attached claims, the phrase "digital display screen" refers to electronic display mechanisms including, without limitation, liquid crystal display (LCD), gas plasma, cathode ray tube (CRT), and others known in the field of digital displays. Also, as used throughout this specification and the attached claims, the term "doctor" refers to anyone using an embodiment of this invention for optometric examinations. The terms "patient" or "VDT user" refer to anyone being examined through an implementation of this invention.

This invention affords a doctor significant flexibility by using a programmable digital display screen. The programmable digital display screen enables the doctor to select an image based on a particular patient's needs. Also, because a digital display screen is made up of pixels that present an approximately Gaussian light distribution, the digital display screen provides viewing conditions virtually identical to those experienced in the particular work environment of the VDT user. This characteristic affords an extremely accurate simulation of typical VDT user eye strain, and it does so in the controlled environment of the doctor's preferred examining location. Of course, to be an effective testing tool, the off-axis angle must be reduced as much as practicable so that the doctor can examine the patient from a point substantially along the line of sight from the patient to the digital display screen. Also, the distance from the patient to the digital display screen must be representative of the distance from the patient to the VDT under typical use. One implementation of this invention includes situating a patient a representative working distance from a desktop, laptop, or palmtop computer screen (or from any other device having a digital display screen). While having the patient focus on images on the computer screen, the doctor can use a retinoscope to evaluate the patient's focusing response from a point substantially along the line of sight from the patient to the digital display screen.

Although using a desktop, laptop, or palmtop computer represent alternative embodiments of this invention, they are not preferred embodiments. A preferred embodiment includes a vision tester apparatus with a programmable digital display screen specifically for use in practicing the invented method in an economical, reliable, compact, and simple-to-operate form.

In a preferred embodiment, the vision tester can display text and graphical images that are either pre-stored in the vision tester or sent from a computer to the vision tester during the examination. The vision tester can include a light source that illuminates the digital display screen, and the digital display screen can be either a monochrome or a color display. The pixel pitch of the digital display screen can be selected to match the viewing conditions of any type of VDT. Furthermore, textual images can display characters in a variety of type fonts and styles used by VDTs. Because this invention uses a digital display screen, the pixels comprising images used in conducting the vision exam exhibit an approximately Gaussian light distribution virtually identical to that experienced by a patient using a VDT in that patient's work environment. Accordingly, unlike with prior vision testers, an embodiment of this invention requires no special construction or components or design in order to diffuse the light to create an approximately Gaussian pattern artificially.

The digital display screen is driven by digital display screen control electronics. The control electronics provide timing and color data to the digital display screen and act as an interface to a frame buffer. The frame buffer holds images that are to be displayed on the digital display screen during operation of the system. These images can consist of any appropriate mix of text and graphics. The graphics can include pictures without accompanying text for allow examination of young patients or patients who do not read well. Furthermore, text images can be in any language. The images to be displayed can be stored in several different forms including pre-loaded ROM, or RAM that is driven from a computer input device. The image to be displayed is determined by the doctor.

A computer input device can connect a computer to the vision tester by any number of methods currently know in the computing art, including, without limitation, standard VGA cables or any of several digital interfaces now being supplied on the market. Microcontroller electronics control the operation of the unit. In the simplest form, the microcontroller electronics could include FPGA that reads control switches to take appropriate action (such as displaying a particular image or dimming a display). In a more versatile form, the microcontroller electronics could include a microprocessor and appropriate RAM and ROM. The microcontroller electronics send a signal to the frame buffer to select a display image, to the backlight to set a dimming level, and to the computer input device to facilitate the computer interface operation. The doctor has controls to turn the system on or off, select the desired image, and control the brightness of the digital display screen. These controls can include switches on the vision tester, or they can be on a connected computer.

The vision tester can be powered through various mechanisms. One example would include either a disposable or rechargeable battery unit. The vision tester can be constructed so that a rechargeable battery unit can either be removed from the vision tester for charging or charged while still inside the vision tester. Another example of a power source would include a plug for connecting the vision tester directly to a wall outlet.

A vision tester embodying this invention also solves the problem of accurate examination by allowing a doctor to reduce significantly the off-axis angle and examine a patient from a point substantially along the line of sight from the patient to the digital display screen. In the case of a computer screen, this could be accomplished by selecting a computer screen with a sufficiently small border. In a preferred embodiment, this is accomplished by constructing the vision tester specifically to reduce the distance between the test image and the position at which the retinoscope is placed to examine the patient's eyes. One such construction provides an aperture within the digital display screen through which the doctor can examine the patient's eyes. As used in this specification and the attached claims, "aperture" is broadly defined as a space through which a doctor can view the patient. An aperture can be a physical hole through the vision tester, a transparent section in the vision tester, or an indentation in the side of the vision tester, such as a recess or sight.

Additional objects and advantages of this invention will be apparent from the following detailed description of a preferred embodiment thereof which proceeds with reference to the accompanying drawings.

DETAILED DESCRIPTION OF A PREFERRED EMBODIMENT

One embodiment of the present invention generally comprises a vision testing method and apparatus for use in optometric examinations to simulate actual viewing conditions encountered by a VDT user and to facilitate prescribing corrective lenses that will perform well for a patient while using a VDT. One feature of this invention solves the problems of providing doctors flexibility and accurately simulating a VDT display by implementing a programmable digital display screen.

This invention has several distinct advantages. First, by providing a programmable vision tester, patients cannot become accustomed to or memorize the images they are to evaluate. By changing the images, the patient is forced to focus on the images in earnest, just as one would when using a VDT. Also, because VDT users constantly have to re-focus their eyes on new or changing images, this programmable vision tester allows a level of examining accuracy that a static-image vision tester cannot provide. Use of programmable images in the vision tester also allows a doctor to achieve, with one system, levels of flexibility and versatility that would have previously required several different vision testers. A doctor can select an image to provide a particular language for someone with poor English skills, symbols or pictures for patient who do not read well, or a simulation of a particular VDT display for a VDT user with particular needs (e.g., a numerical display for a VDT user who does primarily data processing). Together these features provide great flexibility and efficiency while providing a vision test that most accurately simulates the conditions of actual VDT use.

This invention affords a doctor significant flexibility. The programmable digital display screen enables the doctor to select an image based on a particular patient's needs. Also, because a digital display screen is made up of pixels that present an approximately Gaussian light distribution, the digital display screen provides viewing conditions virtually identical to those experienced in the particular work environment of the VDT user.

Figure 1A:
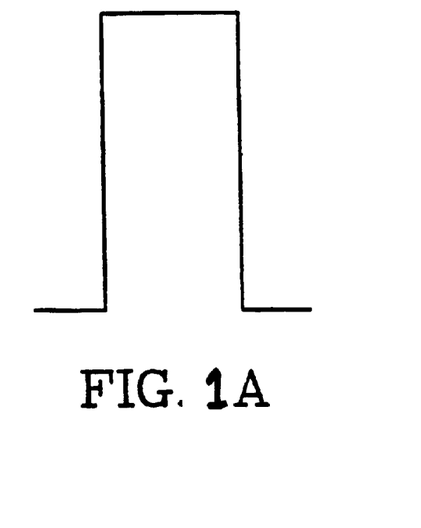
FIG. 1A is a square-wave light amplitude curve illustrative of printed matter and some testing devices of the prior art.
Figure 1B:
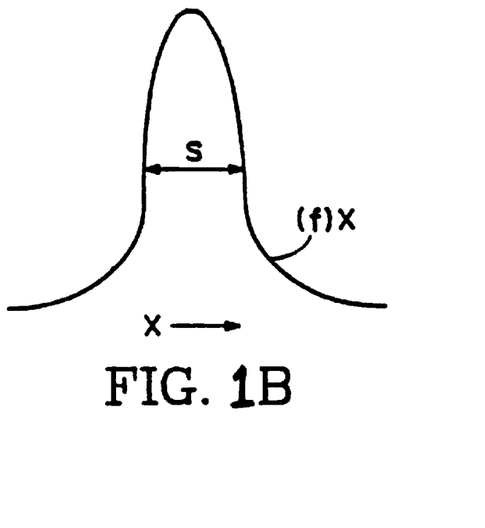
FIG. 1B is a generally Gaussian light amplitude curve approximating that which is expected to be produced by a VDT and an embodiment of the present invention.

If a light meter is scanned across printed characters, they produce a square-wave light amplitude curve as illustrated in FIG. 1A. FIG. 1B is a graph of a Gaussian light amplitude output approximating that provided by a VDT and by an embodiment of the present invention. This curve may be generated by scanning an actual VDT pixel with a micro scan light meter, and it corresponds to the following formula:

$$f(x) = \exp[-(41_n^2 x^2)/s^2]$$

where $1_n$ is the luminance of the pixel, S is the width of the pixel at half luminance maximum and X is the x-axis position of the meter. Previous systems for treating VDT users had to employ an apparatus with a complex layer structure designed to approximate the Gaussian light distribution of FIG. 1B.

Figure 2A:
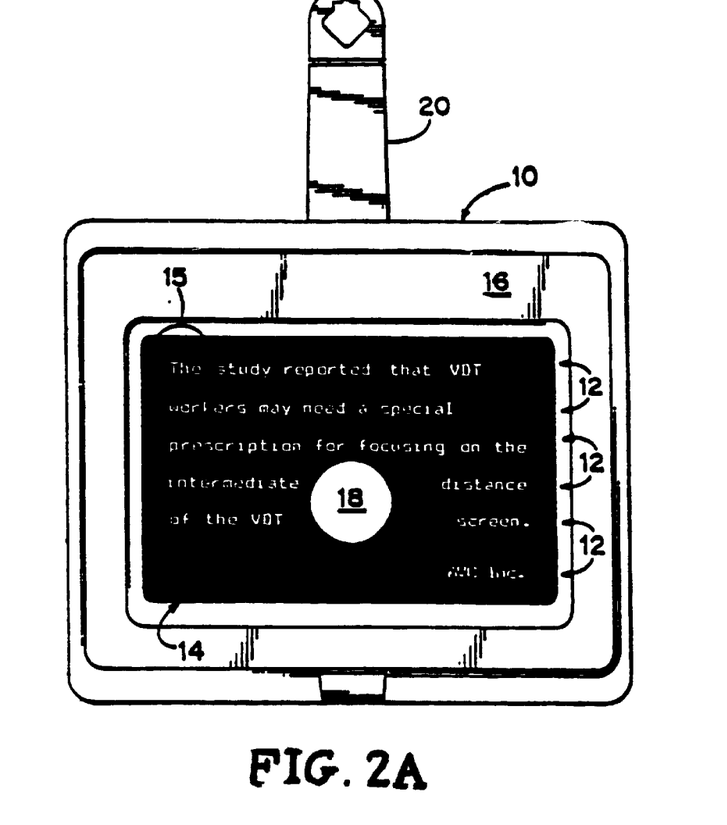
FIG. 2A depicts a static-image vision tester of the prior art.
Figure 2B:
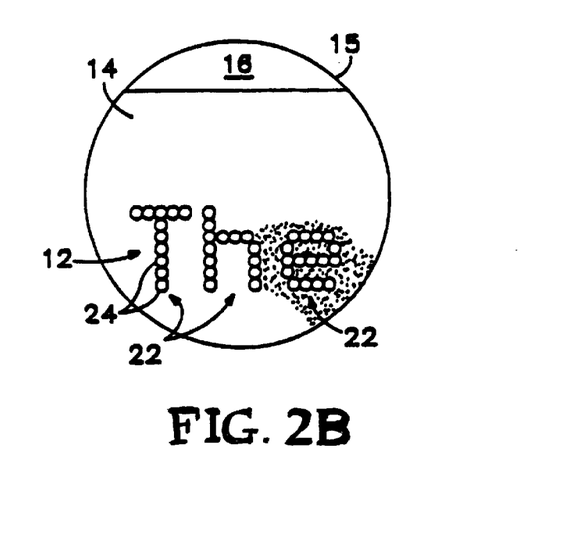
FIG. 2B shows a magnification of the dot-matrix type alphanumeric characters of the prior art vision tester of FIG. 2A.

FIG. 2A illustrates a prior art vision tester apparatus 10 used to artificially simulate a Gaussian light distribution. The apparatus 10 displays static lines of alphanumeric text 12 on a simulated VDT display screen 14. The image on the display screen 14 remains constant and offers doctors little flexibility. Also, as can be seen in the magnification of circle 15 in FIG. 2B, the actual alphanumeric characters 24 comprising the lines of text 12 are constructed of several pixel-like elements 22 disposed in a matrix. In addition to being inflexible, the display of the prior art apparatus 10 poorly represents modern, high-resolution VDT displays. An embodiment of the present invention employs a digital display screen to produce automatically an approximately Gaussian light distribution typical of that which VDT users encounter while using a VDT. This authenticity and accuracy in simulating a VDT display provides a more effective way to prescribe spectacles for VDT users. Also, the flexibility afforded by the programmable display screen in an embodiment of the present invention allows doctors improved efficiency and effectiveness.

Figure 3:
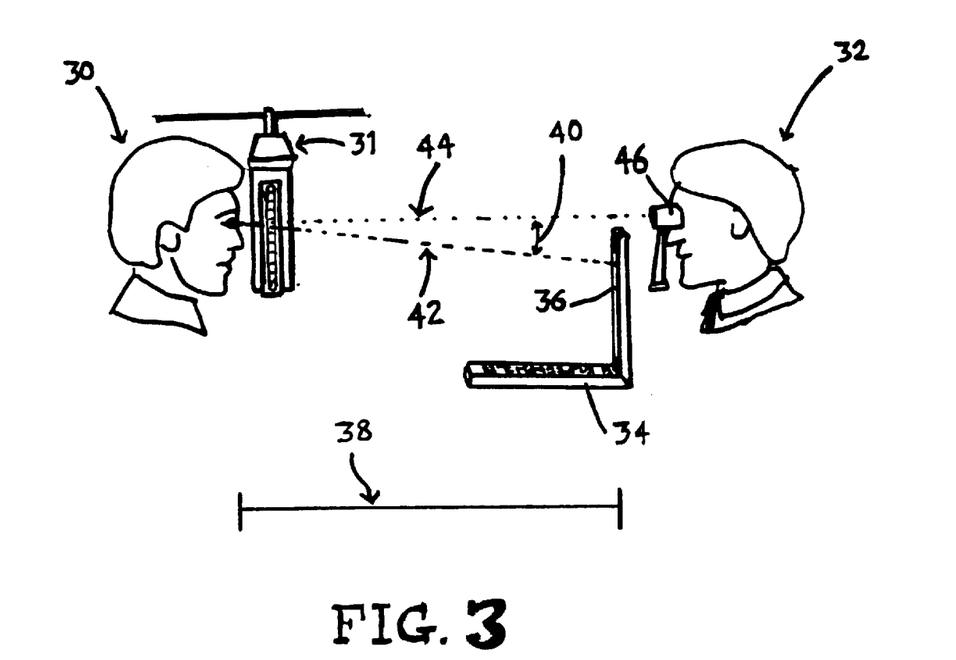
FIG. 3 schematically illustrates an eye examination procedure employing an embodiment of the method of the present invention.

These characteristics allow an extremely accurate simulation of typical VDT user eye strain, and they do so in the controlled environment of the doctor's preferred examining location. Of course, to be an effective testing tool, the off-axis angle should be reduced as much as practicable during an examination so that the doctor examines the patient from a point substantially along the line of sight from the patient to the digital display screen. Also, the distance from the patient to the digital display screen should be representative of the distance from the patient to the VDT under typical use. FIG. 3 illustrates one implementation of this invention, and it includes situating a VDT user 30 a representative working distance 38 from an apparatus 34 with a digital display screen 36. While FIG. 3 presents the use of a laptop computer to supply the digital display screen, other apparatus, such as a desktop or palmtop computer (or any other device having a digital display screen), could also be used. While the doctor 32 has the VDT user 30 focus on images on the display screen 36, the doctor 32 gets as close to the display screen 36 as possible. This is done by minimizing the off-axis angle 40. The off-axis angle 40 is the angle between a line segment 42 from the eyes of the VDT user 30 to the display screen 36 (representing the patient's line of sight), and a line segment 44 from the eyes of the VDT user 30 to the doctor 32. This ensures that the doctor examines the patient from a point substantially along the line of sight from the patient to the digital display screen. Having minimized the off-axis angle, the doctor 32 uses a retinoscope 46 to evaluate the VDT user 30. The doctor 32 can have the VDT user 30 look through a lens changing apparatus, or phoropter 31, as the doctor 32 performs the exam.

Although using a desktop, laptop, or palmtop computer represent alternative embodiments of this invention, they are not a preferred embodiments of this invention for a couple of reasons. First, using an actual computer system often proves awkward, forcing either the patient or the doctor to contort into uncomfortable or unnatural positions in order to obtain the reduced off-axis angle. Also, the off-axis angle is often difficult to reduce due to the large borders on many computer monitors (between the periphery of the display image and the outer edge of the monitor). This does not allow optimal reduction of the distance between the doctor's retinoscope and the patient's focal point on the test image.

It is also less economical to purchase an entire computer system if the primary use of the system is only as a vision tester. Thus, a preferred embodiment includes a vision tester apparatus with a programmable digital display screen specifically for use in practicing the invented method in an economical, reliable, compact, and simple-to-operate form.

A preferred embodiment of the vision tester apparatus can display text and graphical images as required by the needs of the particular VDT user during examination. Text and graphical images are either pre-stored in the unit or may be sent from a computer to the screen during the examination. In a preferred embodiment, the text and graphical images are specially designed with a hole in the images so that the digital display screen can be constructed with an aperture through which the patient's eye can be viewed directly. A preferred embodiment of the vision tester is schematically illustrated in FIG. 4.

Figure 4:
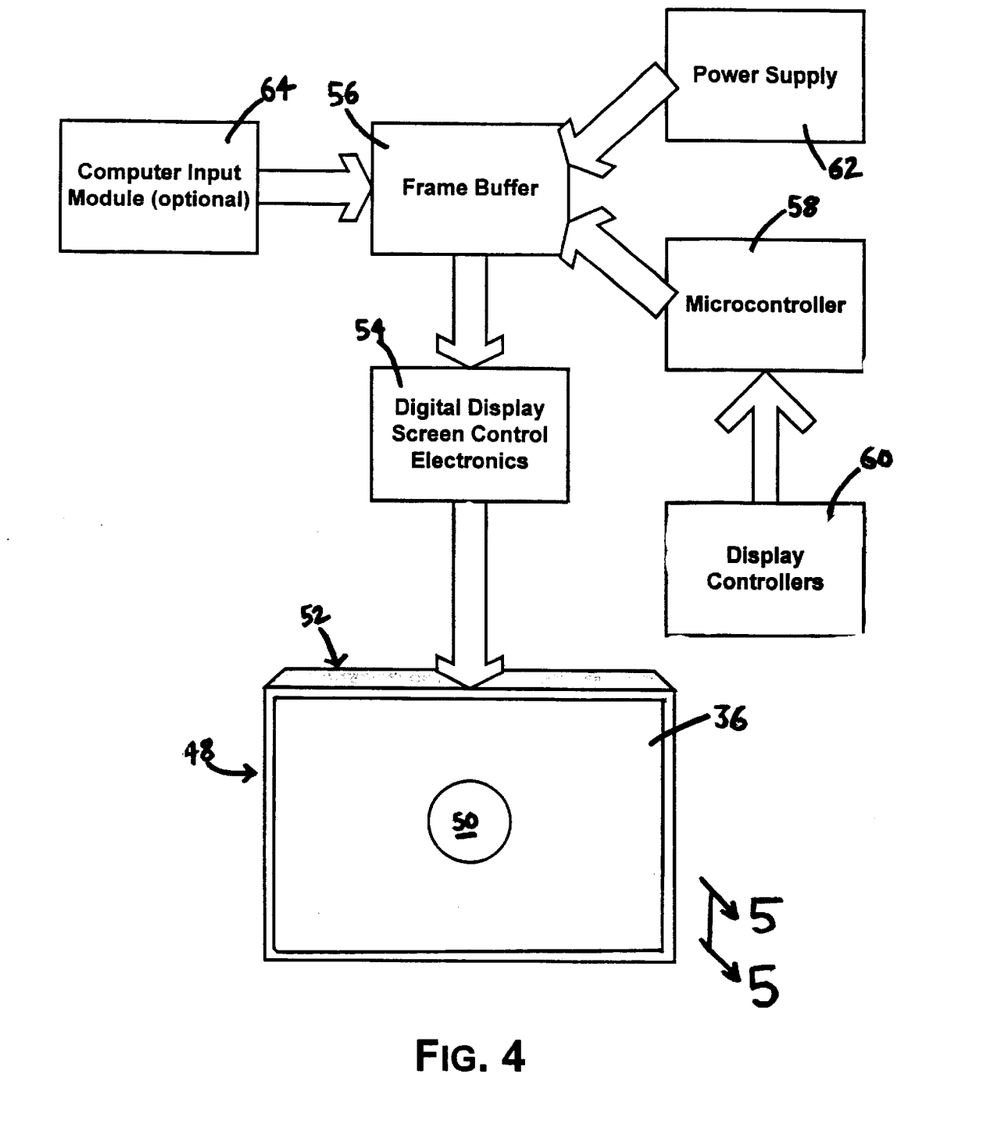
FIG. 4 schematically illustrates an embodiment of the vision testing apparatus of the present invention.

With particular reference to FIG. 4, a preferred embodiment of the vision testing apparatus 48 includes a digital display screen 36 and a backlight 52 that produces white light to illuminate the digital display screen 36. In a preferred embodiment of this invention, the backlight is a generally flat, thick-film electro-luminescent panel. A suitable electro-luminescent panel is commercially available, for example, from Loctite Luminescent Systems, Inc. of Lebanon, N.H. (Part No. LSI RH) or from NEC/World Products Inc. of Sonoma, Calif. (Part No. NEL-5LB-574-W). Any other suitable light source could also be used. Both the backlight 52 and the digital display screen 36 are specially designed to have an aperture 50. The aperture 50 is located so as to reduce the off-axis angle while examining the VDT user. In a preferred embodiment, the aperture 50 is centrally located and consists of a physical hole through the apparatus 48. However, other embodiments include, without limitation, a sight in the digital display screen 36, or a transparency in the digital display screen 36 (without a physical hole).

Figure 5:
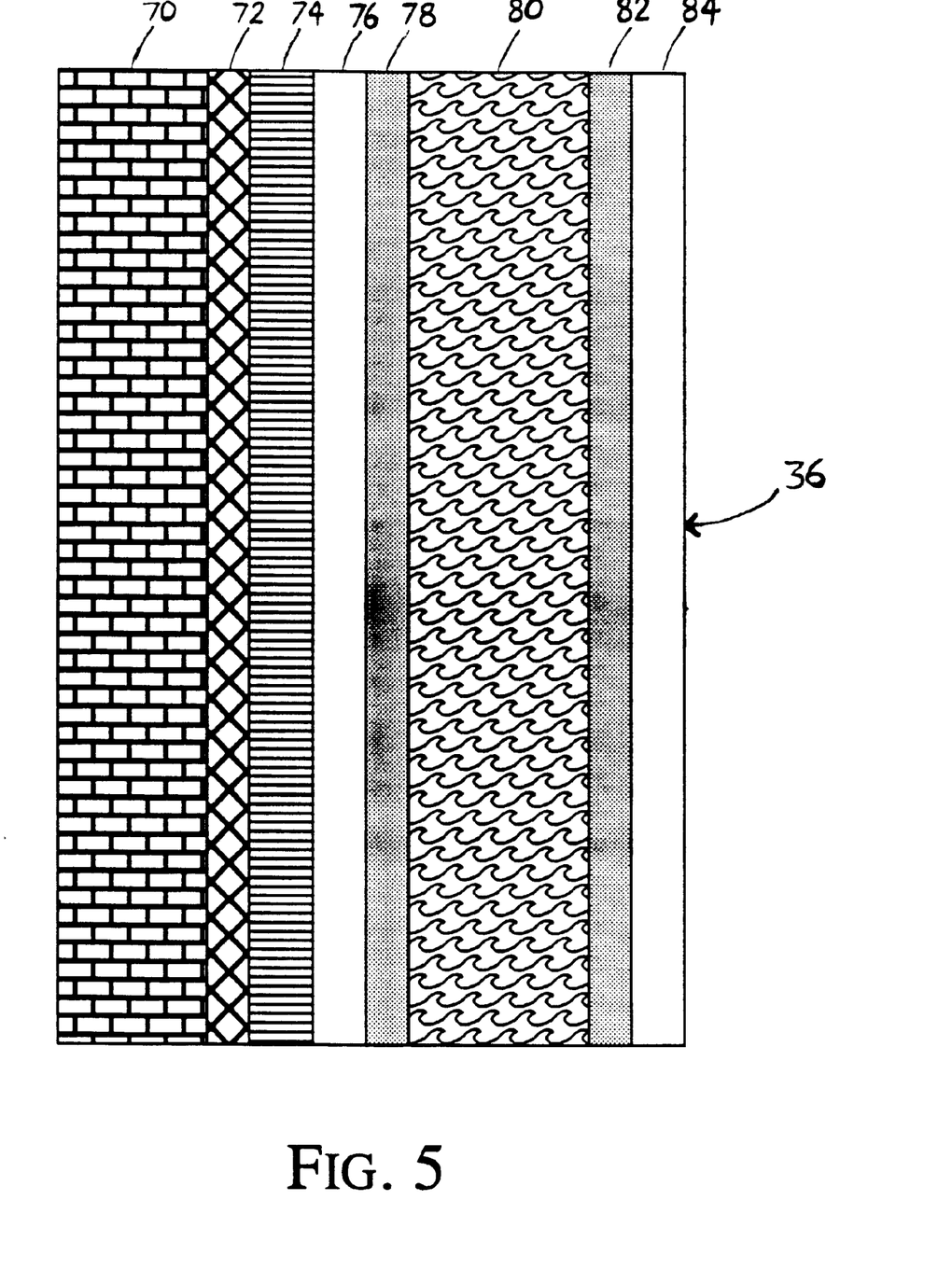
FIG. 5 is an enlarged cross-sectional view of the digital display screen of the vision tester apparatus of FIG. 4, illustrating the multilayered construction of a preferred embodiment.

The backlight is situated behind the digital display screen 36 (from the perspective of a patient viewing the apparatus 48). FIG. 5 shows a cross section of the apparatus 48 and digital display screen 36 of FIG. 4 (viewed from the 5—5 line). A preferred embodiment of this invention uses an LCD panel as the digital display screen. However, various other digital display screens, such as those using gas plasma, CRT, or other technologies known or used in the field of digital displays, could also be used. FIG. 5 shows a preferred embodiment with 8 distinct layers or sections. The actual number, type, or order of these layers could be changed without departing from this invention. In a preferred embodiment, the first layer is an aluminum backing plate 70. The aluminum backing plate 70 is 0.062 inches thick in a preferred embodiment. Next, there is a thin layer of acrylic adhesive 72 for attaching the aluminum backing plate 70 to the backlight 74. Layers 76, 78, 80, 82, and 84 represent a typical LCD digital display screen 36. There are two layers of substantially clear glass 76 and 84. On the inside of each glass layer 76 and 84, there is a thin coating of indium tin oxide (ITO) 78 and 82. Finally, between the ITO layers 78 and 82 there is a reservoir of liquid crystals 80. In a preferred embodiment, the ITO has been removed from area of aperture (50 in FIG. 4), however, an alternative embodiment of the invention can have ITO present.

Again with reference to FIG. 4, the digital display screen 36 may be a monochrome or color display. If there is no physical hole in the display screen 36 to provide the aperture 50, driving the digital display screen 36 to white in the aperture 50 will result in transparency if there is no backlight 52 behind the aperture 50. In a preferred embodiment of this invention using LCD technology, depending on the type of LCD, the polarizer layer of the LCD module may have to be removed in the area of the aperture 50. The pixel pitch of the digital display screen 36 may be selected to match the viewing conditions of any type of VDT display.

The boxes of FIG. 4 exemplify typical elements or components used in the operation of the vision testing apparatus 48. They are depicted for illustrative purposes only. Depending on the particular embodiment of this invention that is adopted, these elements may change. In a preferred embodiment, the digital display screen 36 is driven by the digital display screen control electronics 54. The digital display screen control electronics 54 provide timing and color data to the digital display screen 36 and act as an interface to the frame buffer 56. The frame buffer 56 holds images of the screens that are to be displayed on the digital display screen 36 during operation of the apparatus 48. These images may consist of any appropriate mix of text and graphics. They can also be designed to drive the digital display screen 36 so that the aperture 50 in the digital display screen 36 is driven to white. The frame buffer 56 may consist of a preloaded ROM that contains the images, or it may be RAM that is driven from an optional computer input module 64. The image to be displayed is determined by the operator of the apparatus 48. In the case of the ROM-based system, the operator may scroll through the images using a scroll button located on the apparatus 48. In the case where the frame buffer is driven from a computer, the images to be displayed are controlled by the computer. The actual image selected can be determined by the specific needs of the patient being examined. Images comprising pictures can be used for children or other patients who do not read well, or foreign languages can be used for patients who do not speak English well.

The microcontroller 58 controls the operation of the unit. In the simplest form of a preferred embodiment, this would be a FPGA that reads the display controllers 60 and takes appropriate action in displaying an image or dimming the display. In a more versatile form of a preferred embodiment, it would consist of a microprocessor and appropriate RAM and ROM. The microcontroller 58 sends a signal to the frame buffer 56 to select screen images, to the backlight 52 to set the dimming level, and to the optional computer input module 64 to facilitate the computer interface operation. The memory storage medium employed in embodiments of this invention can comprise semiconductor memory, a magnetic medium, or an optical medium. Examples for preferred memory types include EEPROM, EPROM, PROM, ROM, flash memory, hard disks, floppy disks, CDs, DVDs, PCM/CIA cards, and memory cartridges and tapes.

Figure 6A:
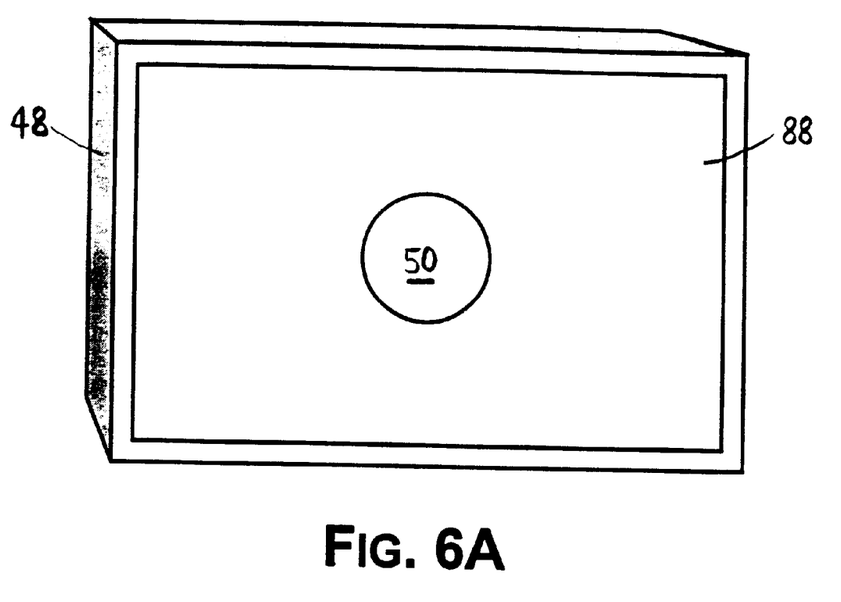
FIG. 6A illustrates a front view of a vision tester where the preprogrammed images and control mechanisms are stored or located within the vision tester.
Figure 6B:
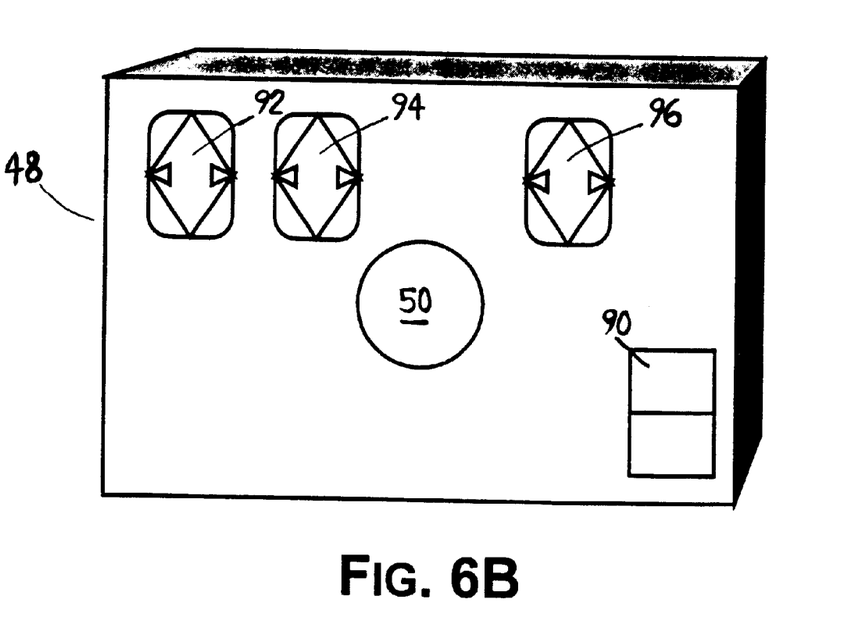
FIG. 6B illustrates a back view of a vision tester where the preprogrammed images and control mechanisms are stored or located within the vision tester.

In a preferred embodiment, the display controllers 60 consist of three switches: on/off, scroll, and brightness controls. FIG. 6A and FIG. 6B illustrate an embodiment of the invention with display controllers on the apparatus 48. FIG. 6A shows the front of the apparatus 48 including the display image 88 upon which the VDT user focuses. FIG. 6B shows the back of the apparatus 48 (the side which the doctor faces) and includes the display controllers. The on/off switch 90 turns the module on or off. The scroll switch 92 allows the doctor to scroll the available screen images, and the brightness control 94 lets the doctor set the brightness of the display. FIG. 6B also shows an optional control switch 96 that could be used to provide any desired functionality to the apparatus 48.

Figure 7A:
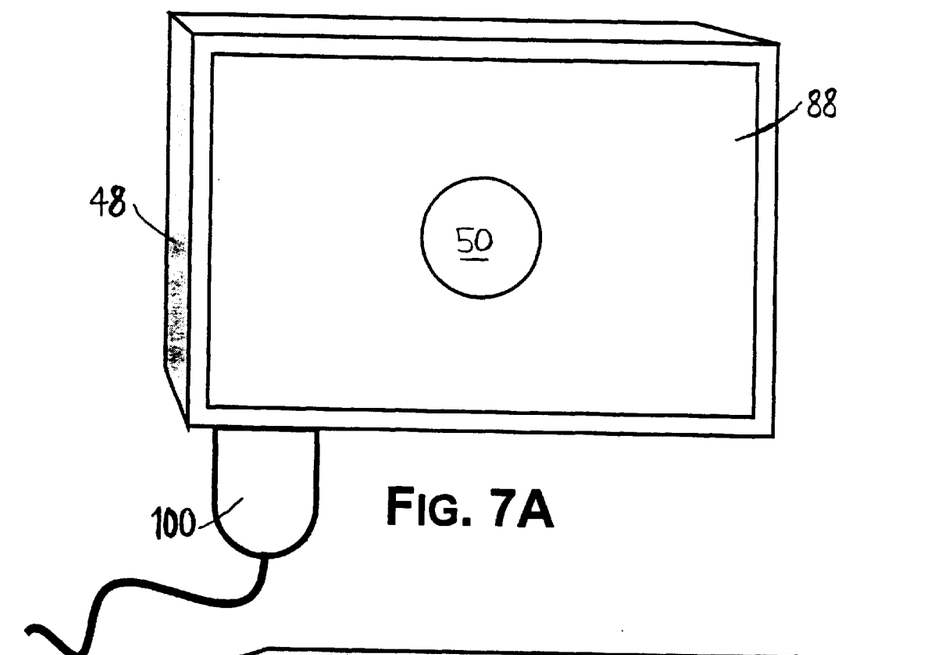
FIG. 7A illustrates a front view of a vision tester where the preprogrammed images and control mechanisms are stored or located external to the vision tester.
Figure 7B:
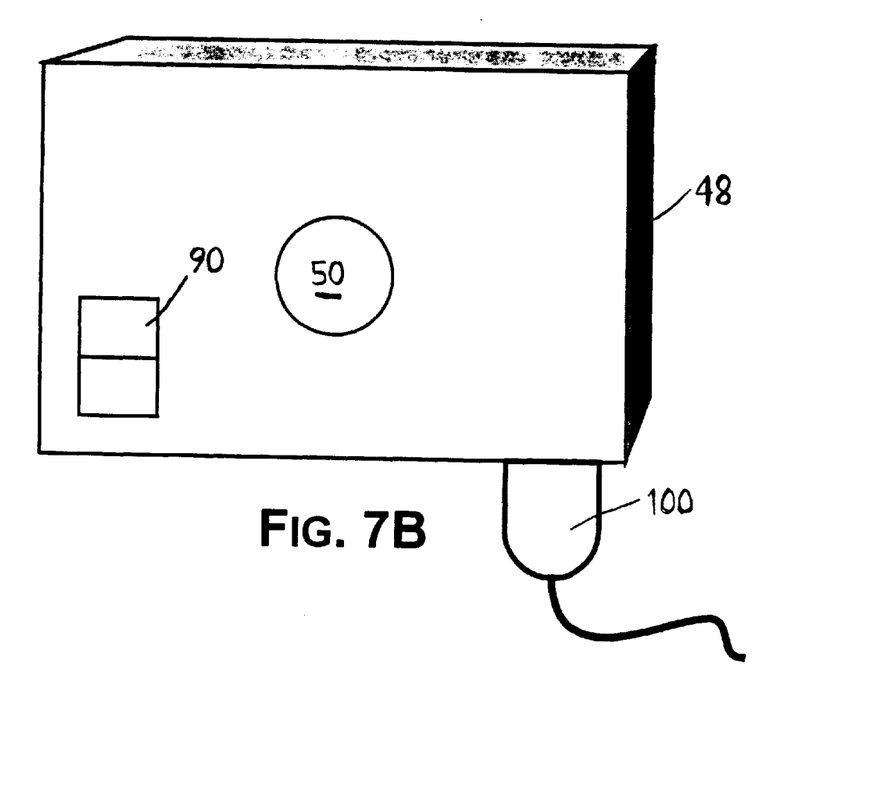
FIG. 7B illustrates a back view of a vision tester where the preprogrammed images and control mechanisms are stored or located external to the vision tester.

FIG. 7A and FIG. 7B respectively illustrate a front and back view of the apparatus 48 embodying the optional computer input module 100. The optional computer input module 100 attaches to the bottom of the apparatus 48 and draws power from the apparatus 48. It interfaces to a computer (not shown) either through standard VGA cables or any of several digital interfaces now being supplied.

Again with reference to FIG. 4, a preferred embodiment of the power supply 62 operates in two modes. It may be run from a rechargeable battery or it may be run from a wall transformer, a DC supply that plugs into an AC outlet. The battery module is removable so that it may charge while a fresh module runs the unit. The battery charging electronics is a separate unit (not shown).

Figure 8A:
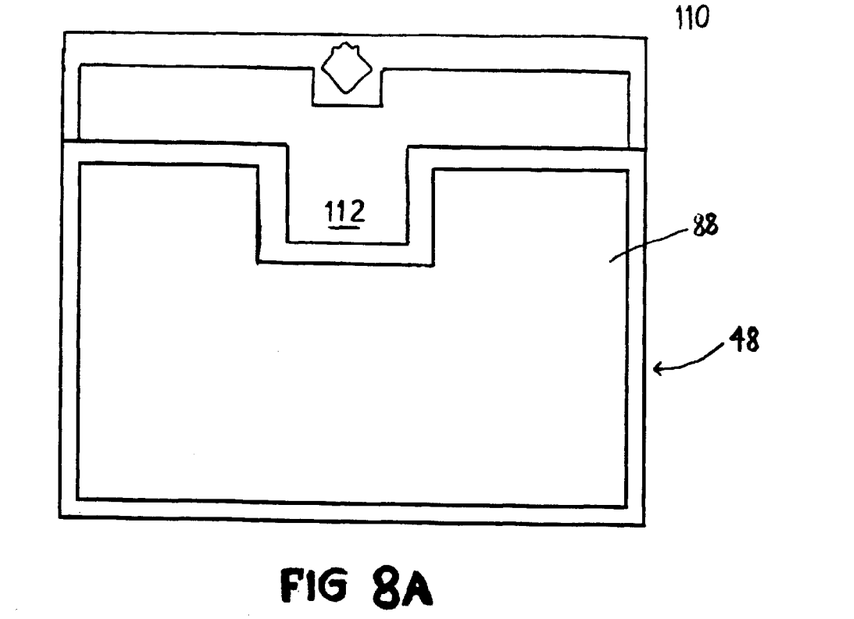
FIG. 8A illustrates an alternative embodiment of a vision tester of the present invention, wherein the aperture is a peripheral indentation or sight.
Figure 8B:
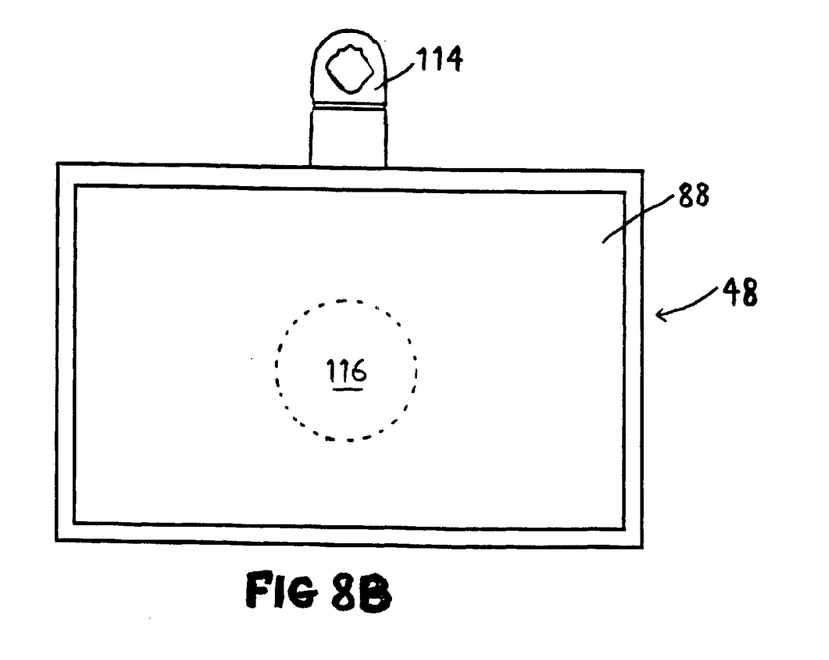
FIG. 8B illustrates an alternative embodiment of a vision tester of the present invention, wherein the aperture is a transparent section.

FIG. 8A and FIG. 8B depict alternative embodiments of the present invention. FIG. 8A depicts the vision testing apparatus 48 incorporating a sight 112 recessed into the perimeter of the apparatus 48 for allowing minimizing the off-axis angle. FIG. 8A also illustrates a mounting module 110 for conveniently mounting the apparatus 48. The mounting module 48 can also be collapsible into the apparatus 48 for easy storage. FIG. 8B shows another embodiment of the apparatus in which the aperture 116 is a transparent section rather than a physical hole in the apparatus 48. FIG. 8B also illustrates an alternative mounting module 114 that can also be collapsed into the body of the apparatus 48 for easy storage of the apparatus 48 when not in use.

Figure 9A:
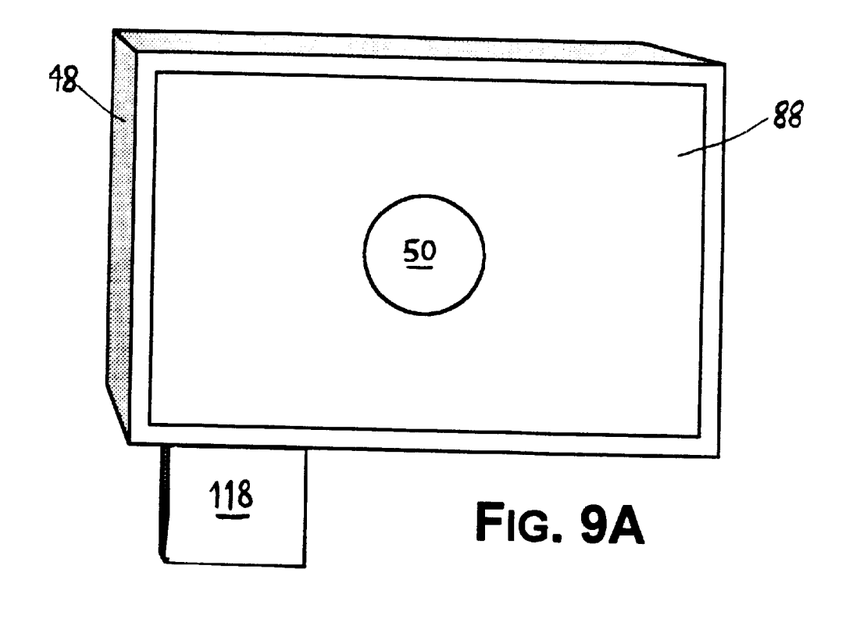
FIG. 9A shows a vision tester apparatus embodying this invention and a removable memory device for storing a preprogrammed image.
Figure 9B:
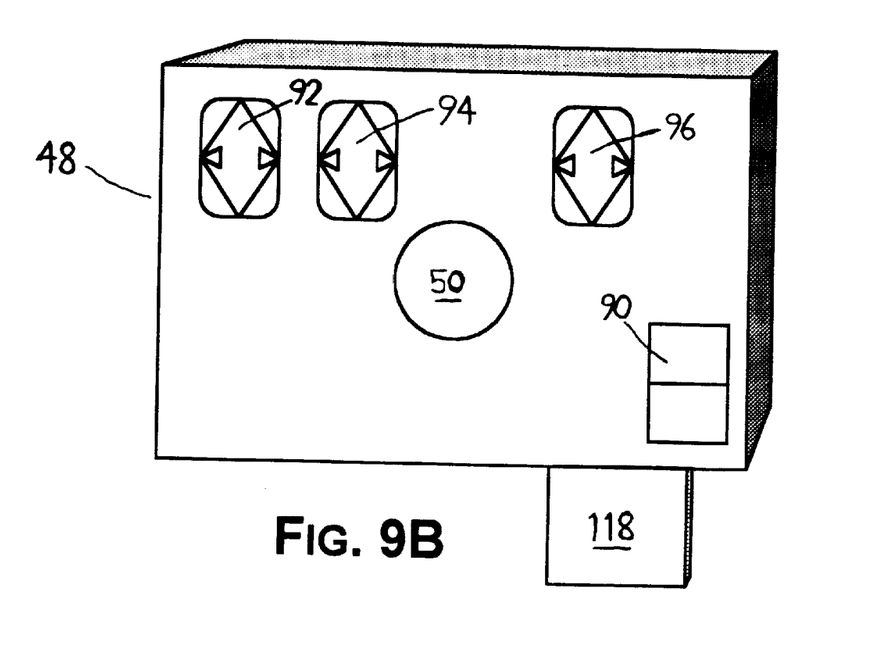
FIG. 9B shows one embodiment of a removable memory device for connection to vision tester apparatus in a manner similar to that illustrated in FIG. 9A.

FIG. 9A depicts a front (patient side) view of another alternative embodiment of a vision tester apparatus along with a connected removable memory device 118 for storing a preprogrammed image. FIG. 9B depicts a back (doctor side) view of the vision tester apparatus of FIG. 9A, with the connected removable memory device 118. The removable memory device 118 can be semiconductor memory, a magnetic memory medium, or an optical memory medium, and it can store data representing a digital image 88 comprising text, graphics, or a combination of both. Also, the text can be in a predetermined language. One vision tester apparatus 48, can interchangeably employ multiple removable memory devices 118, and each removable memory device 118 can represent a different display image 88. FIG. 9B also depicts an on/off switch 90, an image scroll button 92, a brightness controller 94, and an optional controller 96. Both FIG. 9A and FIG. 9B also illustrate an aperture 50.

Figure 10:
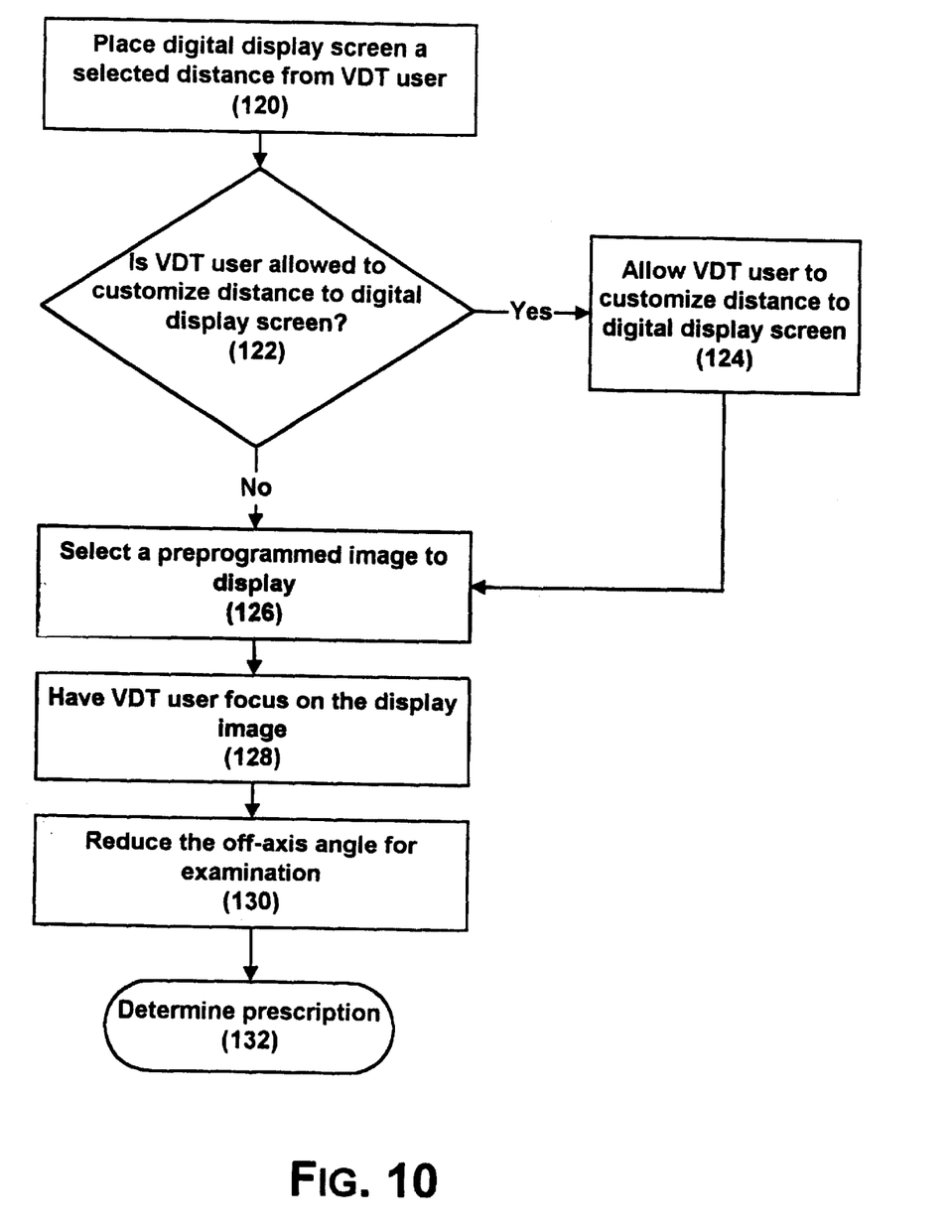
FIG. 10 is a flowchart illustrating a process embodying the method of the present invention.

FIG. 10 depicts the steps involved in a preferred embodiment of the method for prescribing spectacles for VDT users. Certain steps could be omitted, or other steps could be added to customize the process according to the particular preferences or needs of individual doctors or VDT users. In a preferred embodiment, the process begins with a placement step 120 in which a digital display screen is placed a selected distance from the VDT user. Next, there is a customization step 122 in which the VDT user may be allowed to customize the distance to the digital display screen. The customization step 122 allows the VDT user better to simulate actual working conditions. If the VDT user is allowed to customize placement, the VDT user can adjust the distance to the digital display screen 124. After the VDT user customizes the distance 124, or if the VDT user is not permitted to customize the distance, the next step involves selecting a preprogrammed display image 126. The particular display image selected can depend on the individual needs or preferences of the VDT user. Next, the doctor has the VDT user focus on the display image 128, and the doctor reduces the off-axis angle 130. Finally, the doctor conducts the examination and determines an accurate prescription 132 for the VDT user.

Having illustrated and described the principals of our invention in a preferred embodiment thereof, it should be readily apparent to those skilled in the art that the invention can be modified in arrangement and detail without departing from such principles. We claim all modifications coming within the spirit and scope of the accompanying claims.

What is claimed is:

1. A programmable vision tester for use in an optometric examination of a patient, comprising:

an image selector for selecting a preprogrammed image;

a frame buffer for temporarily storing the selected preprogrammed image;

a digital display screen for displaying the selected preprogrammed image, the digital display screen including an aperture substantially aligned with a line of sight from the patient to the selected preprogrammed image so as to provide a doctor a substantially unobstructed view of the patient, wherein the digital display screen includes a transparent section defining the aperture therein;

a light source for illuminating the digital display screen; and a power source for supplying power to the programmable vision tester.

2. A programmable vision tester for use in an optometric examination of a patient, comprising:

an image selector for selecting a preprogrammed image, wherein the preprogrammed image includes a textual character;

a frame buffer for temporarily storing the selected preprogrammed image;

a digital display screen for displaying the selected preprogrammed image, the digital display screen including an aperture substantially aligned with a line of sight from the patient to the selected preprogrammed image so as to provide a doctor a substantially unobstructed view of the patient;

a light source for illuminating the digital display screen; and a power source for supplying power to the programmable vision tester.

3. The programmable vision tester of claim 2, wherein the textual character is in a preselected language.

4. A programmable vision tester for use in an optometric examination of a patient, comprising:

a digital display screen including an aperture substantially aligned with a line of sight from the patient to the digital display screen so as to provide a doctor a substantially unobstructed view of the patient, wherein the digital display screen includes a transparent section defining the aperture therein;

an input port for receiving a removable memory device storing a preprogrammed image; and means for reading the preprogrammed image stored on the removable memory device.

5. An optical examination method for use in examining a patient, comprising:

placing a digital display screen a selected distance from the patient, the selected distance corresponding to the patient's work environment;

adjusting the distance to the digital display screen to simulate working conditions of the patient;

selecting a preprogrammed image to display on the digital display screen;

displaying the selected preprogrammed image on the digital display screen;

having the patient focus on the digital display screen; and examining an eye of the patient substantially along a line of sight from the patient to the selected preprogrammed image.

6. An optical examination method for use in examining a patient, comprising:

placing a digital display screen a selected distance from the patient, the selected distance corresponding to the patient's work environment;

selecting a preprogrammed image to display on the digital display screen displaying the selected preprogrammed image on the digital display screen;

having the patient focus on the digital display screen; and examining an eye of the patient substantially along a line of sight from the patient to the selected preprogrammed image;

wherein the step of selecting a preprogrammed image is based on an individual need of the patient.

7. An optical examination method for use in examining a patient, comprising:

placing a digital display screen a selected distance from the patient, the selected distance corresponding to the patient's work environment;

selecting a preprogrammed image to display on the digital display screen;

displaying the selected preprogrammed image on the digital display screen;

having the patient focus on the digital display screen; and examining an eye of the patient substantially along a line of sight from the patient to the selected preprogrammed image;

wherein the examining step includes examining the eye of the patient through an aperture within the digital display screen.

* * * * *